(12) United States Patent
Shinitzky

(10) Patent No.: US 6,872,712 B1
(45) Date of Patent: Mar. 29, 2005

(54) CYCLIC GLYCEROPHOSPHATES AND ANALOGS THEREOF

(75) Inventor: Meir Shinitzky, Rehovoth (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 09/937,386

(22) PCT Filed: Mar. 24, 2000

(86) PCT No.: PCT/IL00/00184

§ 371 (c)(1),
(2), (4) Date: Jan. 8, 2002

(87) PCT Pub. No.: WO00/57864

PCT Pub. Date: Oct. 5, 2000

(30) Foreign Application Priority Data

Mar. 25, 1999 (IL) ................................. 129179

(51) Int. Cl.$^7$ ........................... A61K 31/66; C07F 9/02; A61P 35/00
(52) U.S. Cl. ........................................ 514/105; 558/73
(58) Field of Search ................................ 514/105, 101; 558/73

(56) References Cited

U.S. PATENT DOCUMENTS 5,565,439 A 10/1996 Piazza et al.

FOREIGN PATENT DOCUMENTS

WO    WO 00/09139 A2    2/2000

OTHER PUBLICATIONS

Chabrier et al. 1975, CAS: 82:56871.*
Yasuda et al., 1981, CAS: 94: 175602.*
Quin et al., 1991, CAS: 115: 29459.*
Eto et al., 1981, see CAS: 95: 75384.*
Yasuda et al., 1982, CAS: 97: 163550.*
(6) Kobayashi et al., 1997, CAS :126 :220705.*
Database Chemabs 'Online! Chemical Abstracts Service, Columbus, Ohio: for JP 09 025235, Kobayashi et al., "Tumor metastasis inhibitors containing 1–0–acylglycerol–2, 3–phosphates", Jan. 28, 1997.
Database Chemabs 'Online! Chemical Abstracts Service, Columbus, Ohio: for JP 07 258278, Kobayashi et al., "Preparation of 1–0–acylglycerol–2, 3–phosphates and DNA polymerase.alpha. inhibitors containing them", Oct. 9, 1995.
Database Chemabs 'Online! Chemical Abstracts Service, Columbus, Ohio: for JP 06 228169, Kobayashi et al., "Method for preparation of 1–0–acylglycerol–2, 3–cyclic phosphate", Aug. 16, 1994.
Database Chemabs 'Online! Chemical Abstracts Service, Columbus, Ohio: for JP 07 149772, Kobayashi et al., "Promoters of protein phosphokinase C activation containing 1–0–acylglycerol–2, 3–cyclic phosphate", Jun. 13, 1995.

D.C. Ayres et al., "The Organic Chemistry of Phosphorus, Part V", *J. Chem Soc*, 1957, pp. 1109–1114.
Monique Revel et al., "Hétérocycles contenant du phosphore", *Org. Magn. Reson.*, 1976, pp. 399–406, vol. 8, No. 8.
M. Shinitzky et al., "Formation of 1,3–Cyclic Glycerophosphate by the Action of Phospholipase C on Phosphatidylglycerol", *The Journal of Biological Chemistry*, Jul. 5, 1993, pp. 14109–14115, vol. 268, No. 19.
T. Ukita, "Organic Phosphates I: Synthesis of 1, 2–Diol Cyclic Phosphates", *Pharm. Bull.*, 1957, pp. 121–126, vol. 5.
Bangying Su et al., "Identification of a Putative Tumor Marker in Breast and Colon Cancer", *Cancer Res.*, 1993, pp. 1751–1755, vol. 53, No. 8.
Steven J. Abbott et al., "Chiral $^{16}$O, $^{17}$O . . . ",*J. Am. Chem. Soc.*, 1978, pp. 2558–2560, vol. 100, No. 8.
Robert K. Boyd et al., "Glycerol 1, 2–Cyclic Phosphate in Centric Diatoms", *J. Biol. Chem.*, 1987, pp. 12406–12408, vol. 262.
N. Clarke et al., "Enzymic Formation of Glycerol 1:2–Cyclic Phosphate", *Biochem. J.*, 1976, pp. 745–747, vol. 153.
Dawson, "Recent Advances in Phosphoglyceride Chemistry", *Ann. Rep. Progr. Chem.*, 1958, pp. 365–376, vol. 55.
Dawson et al., "The Enzymic Formation of *myoinositol* 1: 2–Cyclic Phosphate from Phosphatidylinositol", *Biochem. J.*, 1971, pp. 605–607, vol. 122.
Peter Friedman et al., "Conversion of Lysophospholipids to Cyclic Lysophosphatidic Acid by Phospholipase D", *The Journal of Biological Chemistry*, 1996, pp. 953–957, vol. 271, No. 2.
Eugene P. Kennedy et al., "The Function of Cytidine Coenzymes in the Biosynthesis of Phospholipides", *J. Biol. Chem.*, 1956, pp. 193–214, vol. 222.
Luis F. Leloir, "The Enzymatic Transformation of Uridine Diphosphate Glucose into a Galactose Derivative", *Biochem. Biophys. J.*, 1951, pp. 186–190, vol. 33.

(List continued on next page.)

*Primary Examiner*—Rita Desai
*Assistant Examiner*—Robert Shiao
(74) *Attorney, Agent, or Firm*—Browdy and Neimark, P.L.L.C.

(57) ABSTRACT

Cyclic glycerophosphates as well as some analogs thereof (CGs) are shown to increase phosphorylation of intracellular proteins in various cells. Such activity is not found with linear α or β glycerophosphates. The phosphorylating activity of the CGs render them useful in the prevention and treatment of various disorders and diseases such as, for example, different kinds of malignancies as well as disorders involving hormone and hormone-like signaling. The CGs are also useful for promotion of target cell differentiation and for detection of abnormal conditions in target cells.

30 Claims, 9 Drawing Sheets

OTHER PUBLICATIONS

R. Markham et al., "The Structure of Ribonucleic Acids", *Biochem. J.*, 1952, pp. 552–557, vol. 52.

Meir Shinitzky et al., "Formation of 1, 3–Cyclic Glycerophosphate by the Action of Phospholipase C on Phosphatidylglycerol", *The Journal of Biological Chemistry*, 1993, pp. 14109–14115, vol. 268, No. 19.

M. Mukai et al., "Inhibition of Tumor Invasion and Metastasis by a Novel Lysophosphatidic Acid (Cyclic LPA)", *Int. J. Cancer*, 1999, pp. 918–922, vol. 81.

A. Tomac et al., "Protection and Repair of the Nigrostriatal Dopaminergic System by GDNF in vivo", *Nature*, 1995, pp. 335–339, vol. 373.

T. Ukita et al., "Studies on the Alkaline Hydrolysis of Lecithin: Synthesis of Cyclic 1,2–Glycerophosphate", *J. Biol. Chem.*, 1955, pp. 867–874, vol. 216.

\* cited by examiner

CYCLIC GLYCEROPHOSPHATES AND ANALOGS THEREOF

REFERENCE TO RELATED APPLICATIONS

The present application is the national stage under 35 U.S.C. 371 of international application PCT/IL00/00184, filed Mar. 24, 2000 which designated the United States, and which international application was published under PCT Article 21(2) in the English language.

FIELD OF THE INVENTION

The present invention concerns pharmaceutical compositions comprising cyclic glycerophosphates and analogs thereof and some novel compounds of this type.

PRIOR ART

The following is a list of references which is intended for a better understanding of the background of the present invention.

Boyd, R. K., De Freitas, A. S. W., Hoyle, J., McCulloch, A. W., McInnes, A. G, Rogerson, A. and Walter, J. A., *J. Biol. Chem.*, 262:12406–12408 (1987).
Clarke, N. and Dawson, R. M. C., *Biochem. J.*, 153: pp. 745–747 (1976).
Dawson, R. M. C., *Ann. Rept. Progr. Chem.* 55:365, (1958).
Dawson, R. M. C., Freinkel, N., Jungalwala, F. B. and Clarke, N., *Biochem. J.*, 122:605–607, (1971).
Forrest, H. S. and Todd, A. R., *J. Chem. Soc.*, 1950, 3925, (1950).
Friedman, P., Haimovitz, R., Markman, O., Roberts, M. F. and Shinitzky, M., Conversion of lysophospholipds to cyclic lysophosphatidic acid by phospholipase, *D. J. Biol. Chem.*, 271: 953–957 (1996).
Kennedy and Weiss, *J. Biol. Chem.*, 222:193 (1956).
Leloir, L. F., *Biochem. Biophys., J.*, 33:186 (1951).
Markham, R. and Smith, J. D., *Biochem. J.*, 52:552 (1952).
Shinitzky, M., Friedman, P. and Haimovitz, R., Formation of 1,3-cyclic glycerophosphate by the action of phospholipase C on phosphatidylglycerol, *J. Biol. Chem.*, 268:14109–14115 (1993).
Su, B., Kappler, F., Szwergold, B. S. and Brown, T. R., *Cancer Res.*, 53:1751–1754, (1993).
Tomac, A., et al., *Nature*, 373:335–339 (1995).
Ukita, T., Bates, N. A. and Carter, H. E., *J. Biol. Chem.*, 216:867–874, (1955).

BACKGROUND OF THE INVENTION

L-α-glycerophosphate (αGP), a key constituent in phospholipid metabolism (Kennedy and Weiss, 1956), is abundant in most biological tissues (Dawson, 1958). β-Glycerophosphate (βGP) is a product of enzymatic (Ukita et al., 1955) and alkaline (Clarke and Dawson, 1976) hydrolysis of phospholipids and is formed through the cyclic phosphodiester intermediate 1,2-cyclic glycerophosphate (1,2 cGP) (Ukita et al., 1955; Clarke and Dawson, 1976). 1,2 cGP has been detected in algae species (Boyd et al., 1987) as well as in human cancer tissues (Su et al., 1993). Similarly, αGP can in principle adopt the cyclic form 1,3-cyclic glycerophosphate (1,3 cGP). This compound has been shown to be formed as an intermediate in the phospholipase C hydrolysis of phosphatidyl glycerol (PG) (Shinitzky et al., 1993) and upon further hydrolysis is converted to αGP.

A six-membered cyclic phosphate of foremost biological importance is cyclic AMP. The ring of cyclic AMP is actually a derivative of 1,3 cGP backbone. Other cyclic phosphates which were detected in biological systems include glucose cyclic phosphodiester (Leloir, 1951), 2',3'-cyclic phosphodiester (Markham and Smith, 1952), riboflavin-4',5'-cyclic phosphodiester (Forrest and Todd, 1950), myoinositol-1,2-cyclic phosphodiester (Dawson et al., 1971) and cyclic lysophosphatidic acid (Friedman et al., 1996).

Except for cyclic AMP and cyclic GMP which have been extensively studied, no specific biological activities have been so far assigned to the other biological cyclic phosphates.

List of Compounds and Their Abbreviations

The following compounds which formulas are presented in Appendix A just before the claims, will be represented herein in the specification by their abbreviations as follows:
1. 1,3 cyclic glycerophosphate—1,3 cGP
2. 1,2 cyclic glycerophosphate—1,2 cGP
3. 3-acyl 1,2 cyclic glycerophosphate (cyclic lysophosphatidic acid)—c-lysoPA
4. Phenyl 1,3 cGP—P-1,3 cGP
5. Phenyl 1,2 cGP—P-1,2 cGP
6. 1,3 cyclic propanediol phosphate—1,3 cPP
7. 1,2 cyclic propanediol phosphate—1,2 cPP
8. Phenyl 1,3 cPP—P-1,3 cPP
9. Phenyl 1,2, cyclic propanediol phosphate—P-1,2, cPP
10. Cyclic dihydroxyacetone phosphate—cDHAP
11. Phenyl cyclic dihydroxyacetone phosphate—P-cDHAP Glossary The following is an explanation of some terms used above and in the following description and claims:
CG—the cyclic glycerophosphates and analogs thereof of the invention.
Target cells—cells in which, following contact with the CGs of the invention, there is phosphorylation of intracellular proteins. In some cases, contact of the target cells with CGs results in maturation of the cells and in other cases in hormone-like signaling activities. In addition, a variety of cellular events may occur in the target cells following their contact with the CGs of the invention.
Intracellular phosphorylation (used interchangeably with phosphorylation of intracellular proteins)—rise in the level of phosphorylation in one or more of the intracellular proteins of the target cells following incubation of the cells with the CGs of the invention. The phosphorylation is typically of the tyrosine amino acid in the protein but may also be of the threonine or serine amino acid. The protein may be any protein inside the target cell that can be phosphorylated. Typically the protein in which phosphorylation occurs is constitutively phosphorylated to some extent and the level of its phosphorylation is effected by the CGs. The level of phosphorylation may be determined using any of the methods known in the art such as those described below.
Promotion of cell differentiaton—the activity of the CGs of the invention causing changes in the target cells which are correlated with the differentiation stage of the cells. The changes may be in anatomical characteristics, in the expression of differentiation antigens, etc.
Induction of hormone-like signaling—the activity of the CGs of the invention on target cells which results in changes which are typically induced by hormones. The CGs applied externally to the target cells pass through the cell membrane and exert their effect inside the target cells. For example, in target cells expressing the insulin receptor, such changes may be similar to the effects exerted by insulin on the same cells.

Analog—relates to any compound which is derived from one of the cyclic glycerophosphates of the invention and which substantially maintains the activity of the cyclic glycerophosphate from which it was derived, including, for example, deoxy analogs and phenyl esters of the cyclic glycerophosphates, preferably, deoxy analogs.

Substantially maintaining—this term relates to the analogs ability to promote the activity carried out by the cyclic glycerophosphate from which they were derived to a certain extent. The analog's activity will be considered to be substantially maintained wherein the activity is 30% or above, preferably 50% or above, more preferred 70% or above, and most preferably 90% or above the level of the activity of the cyclic glycerophosphate.

Effective amount—wherein the method of the invention is intended for prevention of a non-desired condition, the term "effective amount" should then be understood as meaning an amount of the active compound which, when administered, results in the prevention of the appearance of the said condition. Prevention of such a condition may be required prior to the appearance of any symptoms of a disease, e.g. in individuals having a high disposition of developing the disease. Wherein the compositions or methods are intended for treatment of an ongoing non-desired condition, the term "therapeutically effective amount" should then be understood as meaning an amount of the active compound which is effective in ameliorating or preventing the enhancement of the treated condition and related symptoms, which reduces the undesired symptoms or which completely eliminates them.

SUMMARY OF THE INVENTION

It has now been found, in accordance with the present invention, that extracellular application of cyclic glycerophosphates and analogs thereof to target cells increases within minutes the level of phosphorylation in intracellular proteins of the cells. Linear αGP and linear βGP on the other hand, lack this activity.

The present invention thus provides, by a first of its aspects, a pharmaceutical composition comprising a pharmaceutically acceptable carrier and, as an active ingredient, a compound of the general formula I:

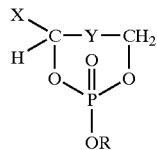

(I)

wherein

Y is —(CH$_2$)$_m$—, —CH(OH)— or —C(=O)—, and m is 0–3;

X is H, alky, —CH$_2$OH—, CH$_2$Oacyl or —CH$_2$acyl; and

R is H, a cation, allyl or optionally substituted aryl.

As used herein the term "alkyl" refers to an alkyl group having from about 1 to about 24 carbon atoms, e.g. preferably from about 3 carbon atoms to about 20 carbon atoms, most preferably from about 5 carbon atoms to about 15 carbon atoms; the term "acyl" refers to an aliphatic saturated or unsaturated C$_1$–C$_{24}$ acyl group, preferably an acyl group having an even number of carbon atoms, most preferably an acyl group derived from a natural fatty acid such as a saturated aliphatic acyl group selected from acetyl, butyryl, caproyl, octanoyl, decanoyl, lauroyl, myristyl, palmitoyl and stearoyl, or an unsaturated aliphatic acyl group selected from palmitoleyl, oleyl, linoleyl, and ricinoleyl; and the term "aryl" refers to a mono- or poly-carbocyclic aryl group, most preferably phenyl, optionally substituted by C$_1$–C$_4$ alkyl, halogen and/or hydroxy. R may be any physiologically suitable cation and is preferably Na$^+$.

In one embodiment, Y is —CH(OH)—, X is H and R is H or phenyl. According to this embodiment, the composition comprises 1,3 cyclic glycerophosphate (1,3 cGP) or phenyl 1,3 cyclic glycerophosphate (P-1,3 cGP).

In another embodiment, Y is —C(=O)—, X is H and R is H or phenyl. According to this embodiment, the composition comprises cyclic dihydroxyacetone phosphate (cDHAP) or phenyl cyclic dihydroxyacetone phosphate (P-cDHAP).

In a further embodiment, Y is —(CH$_2$)$_m$—, m is 0, X is —CH$_2$OH and R is H or phenyl. According to this embodiment, the composition comprises 1,2 cyclic glycerophosphate (1,2 cGP) or phenyl 1,2 cyclic glycerophosphate (P-1,2 cGP).

In still a further embodiment, Y is —(CH$_2$)$_m$—, m is 0, X is a C$_1$—C$_{24}$ alkyl, preferably —CH$_3$ and R is a cation or phenyl. According to this embodiment, the composition comprises 1,2 cyclic propanediol phosphate (1,2 cPP) or phenyl 1,2 cyclic propanediol phosphate (P-1,2 cPP).

In yet still a further embodiment, Y is —(CH$_2$)—, m is 1, X is a C$_1$–C$_{24}$ alkyl, preferably —CH$_3$ and R is a cation or phenyl. According to this embodiment, the composition comprises 1,3 cyclic propanediol phosphate (1,3 cPP) or phenyl 1,3 cyclic propanediol phosphate (P-1,3 cPP).

In yet another embodiment, Y is —(CH$_2$)$_m$—, m is 0, X is —CH$_2$ (C$_1$–C$_{24}$)acyl, preferably oleyl, and R is a cation. According to this embodiment, the composition comprises 3-acyl-1,2 cyclic glycerophosphate (cyclic lisophosphatidic acid—c-lyso PA).

In another aspect, the invention relates to novel compounds of the above Formula I with the exception of the following compounds: (i) compounds wherein Y is —(CH$_2$)$_m$—, m is 0, X is CH$_3$, —CH$_2$OH or CH$_2$Oacyl wherein acyl is a saturated carboxylic acyl with more than 12 carbon atoms, and R is H or a cation; (ii) compounds wherein Y is —(CH$_2$)$_m$—, m is 1, X is H and R is H, a cation or phenyl; and (iii) compounds wherein Y is —CH(OH)—, X is H and R is H, a cation or phenyl.

Examples of the new compounds are the compounds:
phenyl 1,2 cyclic glycerophosphate
phenyl 1,2 cyclic propanediol phosphate
cyclic dihydroxyacetone phosphate
phenyl cyclic dihydroxyacetone phosphate
cyclic oleyl lysophosphatidic acid.

By another of its aspects, the present invention provides a pharmaceutical composition for inducing phosphorylation in intracellular proteins of target cells comprising a pharmaceutically acceptable carrier and, as an active ingredient, a compound of general Formula I above.

Such phosphorylation of proteins is known to be an essential stage of many signaling pathways which are involved in cellular processes. The phosphorylating activity of the cyclic glycerophosphates and analogs thereof of the invention renders them useful in the prevention and treatment of various is disorders and diseases.

The present invention also provides a pharmaceutical composition for treatment of disorders and diseases which can be treated by phosphorylation of intracellular proteins comprising a pharmaceutically acceptable carrier and, as an active ingredient, a compound of general Formula I above.

In addition, the present invention provides a method for treatment of disorders and diseases which can be treated by phosphorylation of intracellular proteins comprising administering to the individual in need a therapeutically effective amount of a compound of general Formula I above.

One cellular process which involves phosphorylation in intracellular proteins is cell differentiation. The present invention also provides a pharmaceutical composition comprising a pharmaceutically acceptable carrier and, as an active material, a compound of the general Formula I above for promotion of cell differentiation in target cells.

The capability of the compositions of the invention to induce cell differentiation in target cells makes them especially suitable for use in the treatment of various disorders and diseases such as various malignancies. In accordance with the invention it was shown, for example, that the cyclic phosphate 1,3 cGP increases the expression of estrogen receptor on breast cancer tumor cells in culture. This makes these compounds good candidates for treatment of breast cancer as well as blood malignancies such as leukemias and lymphomas and other solid tumors such as brain tumors, etc.

By an additional aspect, the present invention also provides a method for the treatment of malignant diseases comprising administering to an individual in need a therapeutically effective amount of the compound of Formula I above.

In addition, due to the capability of the compositions of the invention to induce hormone-like signaling, they may be used for the prevention or treatment of various disorders in which such hormone signaling is involved.

By yet another of its aspects, the present invention provides a pharmaceutical composition comprising a pharmaceutically acceptable carrier and, as an active material, a compound of the general Formula I above for induction of hormone-like signaling.

The hormone-like signaling activity of the pharmaceutical composition of the invention may affect the target cell in a similar manner as that of the typical hormone which affects the cells and/or may be synergistic with the activity of the hormone resulting in an elevated signal in the treated cells. In accordance with this aspect of the invention, the CGs may, for example, be used for induction of an insulin-like signal. This may be useful in the treatment of non-insulin dependent diabetes mellitus (non-IDDM)—type II diabetes. In addition the CGs may be used for induction of the signal of human growth hormone (HGH) in the treatment of disorders in which HGH is involved, for induction of epidermal growth factor (EGF) for use in the treatment of disorders involving EGF, etc.

By yet another of its aspects, the present invention provides a method for the treatment of diseases involving hormone-like signaling comprising administering to an individual in need a therapeutically effective amount of the compound of the Formula I above.

In addition, the compounds of the invention may be used to prepare medicaments suitable for treating diseases and disorders such as those mentioned above.

Being involved in crucial signaling pathway of the cell, the level of phosphorylation of intracellular proteins may be used as an indicator of certain cellular situations. For example, there may be disorders which affect the activity of kinase enzymes or phosphatase enzymes resulting in abnormal levels of phosphorylation in response to extracellular stimulations. By contacting cells of interest with the CGs of the invention, it is possible to measure the level of phosphorylation in the cells and to compare it to the level of phosphorylation in normal cells. A level of phosphorylation which differs from that in normal cells may indicate an abnormal condition in the tested cells. Thus, the present invention also provides a method for detecting abnormal conditions of a tested cell comprising:

i. contacting the cells with a CG of the invention;
ii. detecting the level of phosphorylation in intracellular proteins of the tested cells; and
iii. comparing said level of phosphorylation to the level of phosphorylation in intracellular proteins of normal cells following their contact with said CGs, a level of phosphorylation differing from that detected in the normal cells indicating a high probability of abnormality in the tested cells.

BRIEF DESCRIPTION OF THE FIGURES

FIG. 10A shows phosphorylation of the 117 kD band of the insulin receptor and FIG. 10B shows phosphorylation of the 200 kD band of the insulin receptor.

DETAILED DESCRIPTION OF THE INVENTION

Figure 1:
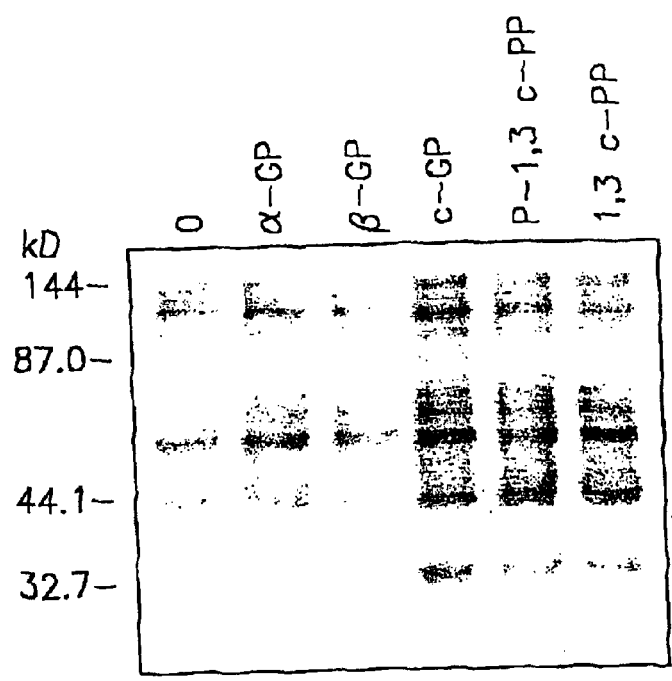
FIG. 1 shows the level of tyrosine phosphorylated proteins in CHO cells after 1 min. pulsing at 37° C. with 1 $\mu$M αGP, βGP, 1,3 cGP (E), P-1,3 cPP and 1,3 cPP. Detection with polyclonal anti-phosphotyrosine antibodies.

In accordance with the present invention it has been found that cyclic glycerophosphates and some of their analogs (all herein designated "CGs"), are involved in signaling pathways in cells. Linear ca and b glycerophosphates do not exert such an activity.

Cyclic glycerophosphates can be formed by enzymatic degradation of phospholipids which in most cases yields five or six membered ring cyclic phosphates. The present invention encompasses within its scope both such cyclic glycerophosphates formed by enzymatic degradation of phospholipids as well as synthetically formed ones. CGs having rings of less than five or more than six carbon atoms are also included within its scope.

The cyclic glycerophosphates and analogs of the invention may generally be synthesized using any one of the methods known in the art for synthesis of phosphate esters. Specific methods which may typically be used for preparing the cyclic phosphates of the invention are described specifically below (see Examples).

Analogs of these cyclic glycerophosphates of the invention are also within the scope of the invention being typically deoxy analogs as well as phenyl esters of the 1,3 cyclic phosphates. These analogs may also be prepared by enzymatic methods or synthetically by any of the methods known in the art In addition to the active ingredient, the pharmaceutical compositions of the invention may also contain a carrier selected from any one of the carriers known in the art. The nature of the carrier will depend on the intended form of administration and indication for which the composition is used. The compositions may also comprise a number of additional ingredients such as diluents, lubricants, binders, preservatives, etc.

The signaling activity of the CGs of the invention is exerted through their capability to induce phosphorylation of intracellular proteins in cells. When the CGs are applied onto the cells, a rapid phosphorylation is observed in intracellular proteins. Typically, the phosphorylating activity of the CGs may be observed after a period of between about 0.5 mins. to about 20 mins. of contact with the target cells.

In accordance with the invention, the phosphorylating activity of the CGs may be measured by any of the methods known in the art. Generally, following incubation of the CG with the target cells, the cells are lysed, the protein concentration in each sample is determined and the level of phosphorylation of the proteins is determined using known methods and suitable and available polyclonal or monoclonal antibodies. Typically, phosphorylation occurs on the tyrosine residues of the protein and such phosphorylation is determined using either polyclonal or monoclonal anti phosphotyrosine antibodies (such as those described below in the Examples). However, in some cases, phosphorylation occurs on the threonine or serine components of the proteins in which case polyclonal or monoclonal anti phosphothreonine or anti phosphoserine antibodies may be used.

The molecular weight of the proteins in which phosphorylation occurs following incubation with various kinds of CGs may also vary to a certain extent. Thus, for example, incubation of CHO and NIH-3T3 cells with six membered ring cyclic phosphates resulted in phosphorylation of proteins having a molecular weight of about 35 kD, about 45 kD, about 60–70 kD and about 120 kD. The molecular weight of the proteins found to be phosphorylated following incubation of the same cells with five membered ring cyclic phosphates was about 18 kD, about 35 kD and about 38 kD.

The CGs of the invention may be administered to cells in vitro. Such administration may result in desired changes in the cells which may then be administered back to an individual in need. In addition, administration of the compositions to cells may result in enhanced secretion of various growth factors by these cells which, in turn, could also be used for treatment of various conditions alone or in combination with other CGs of the invention.

The effective amount of the CG to be used in vitro in accordance with the invention may vary in accordance with the nature of the CG as well as the target cells and can easily be determined by a person versed in the art by using any of the above-mentioned methods or any of the methods known in the art. For in vitro induction, the typical range of concentration of CG needed to induce phosphorylation is between about 0.5 μm to about 10 μM.

Many cellular processes are triggered by protein phosphorylation (mostly tyrosine phosphorylation). Thus, application of the CGs to target cells results in various cellular processes. One such process, is cell differentiation. Such differentiation may easily be determined by a person skilled in the art by measurement of parameters and characteristics in the target cells upon their differentiation. The CGs capability of inducing differentiation of cells makes them useful in the prevention or treatment of disorders or diseases in which differentiation of cells is desired such as, for example, in various malignant diseases.

The CGs of the invention are also able to exert hormone-like signaling activities in target cells. Thus, for example, the CGs of the invention may exert insulin-like activity on cells expressing the insulin receptor. This makes the CGs of the invention suitable candidates for treatment of disorders or diseases involving hormone signaling. The CGs of the invention may also be used in synergism with known hormones, e.g. together with insulin in the treatment of IDDM.

Where the compositions of the invention are administered in vivo, a preferred mode of their administration is either i.v., topically or per os although at times it may be advantageous to use other administration modes as well.

Typically, the pharmaceutical compositions of the invention will comprise about 1 mg to about 10 mg of the active material per kg body weight of the treated individual.

While the compositions of the invention will typically contain a single CG, it is possible at times to include in the composition or to co-administer two or more CGs which may then act together in a synergistic or additive manner to prevent or treat the specific disorder.

According to the invention, the CGs may be administered either in a single dose or may be given repetitively over a period of time.

The compositions of the invention may also be administered to the treated individual in combination with an additional treatment, e.g. wherein the treated condition is a malignant one, the compositions may be given together with one of the currently available drugs or therapies used for treatment of such diseases such as various chemotherapeutic drugs together with a growth factor such as Interleukin-2 (IL-2). In another example, the CGs of the invention may be administered to an individual suffering from IDDM in combination with insulin. In such a combination treatment the CGs may be administered simultaneously with or at different times than the administration of the additional treatment so as to yield a maximum preventive or therapeutic effect.

The induced increase in intracellular phosphorylation by cyclic phosphates of the invention may be the result of the effect of the cyclic phosphates on one of several routes including activation of intracellular kinases (e.g. MAPK) on the one hand and inhibition of phosphatase activity on the other hand. Each of the above routes which may occur separately or in combination results in the augmentation of the degree of phosphorylation of intracellular proteins. The apparent degree of phosphorylation of such proteins is, most likely, at a steady state between counteracting kinase and phosphatase activities.

Without being bound by theory, and on the basis of the results of the present invention, the CGs of the invention may exert their activity in the following way: upon application of the cyclic phosphate to the target cell, the CG first partitions into the cytosol of the cell and when it reaches certain local concentration (of between about 0.1 to about 1 $\mu$M) is capable of activating kinases in the cytosol (such as MAPK). At the same time the CGs also inhibit phosphatase activity. The activation of kinases and inhibition of phosphatase activity results in induction of phosphorylation of tyrosine or serine/threonine phosphorylations in a series of proteins. As the concentration of the CGs in the cytosol rises, phosphodiester activity cleaves the active cyclic phosphates reducing their above activities and resulting in a reduction in the phosphorylation level of proteins in the cells.

The cyclic phosphates of the invention may be used in any of their isomer forms. For various purposes, one of the isomers may be preferred over the remaining ones. For example, amongst the four stereo isomers which constitute the synthetic 1,3 cGP depicted in Appendix A, the enzymatic product 1,3 cGP(E) is preferred for use for inhibiting the overall intracellular phosphatase activity.

EXAMPLES

The invention will now be illustrated by the following non-limiting examples with reference to the appended figures.
Chemical Section
Synthesis of the Cyclic Phosphates The cyclic phosphates of the invention are prepared by the reaction of a suitable dihydroxy compound wherein Y is —$(CH_2)_m$— or —C(=O)— and X is H or alkyl with phosphorus oxycloride ($POCl_3$) when R is H or with aryl, e.g. phenyl, phosphorodichloridate (RO—P(=O)$Cl_2$) when R is aryl.

When there is one or more hydroxy groups in the starting compound, namely Y is —CH(OH)— and/or X is —$CH_2OH$—, these hydroxy groups have to be protected, e.g. by benzylation, and the benzyl group is then removed after cyclization by conventional catalytic hydrogenation in the presence of a suitable catalyst such as Pt or Pd.

The reaction is carried out in an anhydrous solvent, e.g. dioxane or methylene chloride, in the presence of equivalent amounts of a nucleophile such as pyridine or triethylamine. The end products, when R is not aryl, are usually obtained as salts. The synthesis of a series of known and novel 5- and 6-membered ring cyclic phosphates is illustrated below.

Example 1

Synthesis of 1,3 Cyclic Glycerophosphate (1,3 cGP) and 1,3,cGP(E)

The procedure of Buchnea (Buchnea, 1973) was followed essentially as described. Briefly, 2-benzyloxy-1,3-propanediol (Aldrich) was reacted with an equimolar amount of phosphorus oxychloride (Aldrich) in methylene chloride. The resulting 2-benzyl-1,3 cGP was treated with hydrogen under the catalysis of Pd black in methanol to remove the benzyl residue. The 1,3 cGP, isolated as the Ba salt, was pure on paper chromatography (n-propanol: ammonia: water 6:3:1, $R_f$=0.52).

1,3 cGP was also produced by the cleavage of phosphatidyl glycerol (PG) with phospholipase C as described (Shinitzky et al., 1993). The product, termed 1,3,cGP(E) had a trace of approx. 10–20% α-GP as indicated by paper chromatography.

Example 2

Synthesis of 1,2 Cyclic Glycerophosphate (1,2 cGP)

This compound was prepared as described (Kugel and Halmann, 1967). The disodium salt of β-glycerophosphate (Sigma) was first converted to the acid form and then cyclized with dicyclohexylcarbodiimide (Aldrich). The product, isolated as the Ba salt, was pure on paper chromatography.

Example 3

Synthesis of Phenyl 1,3 Cyclic Glycerophosphate (P-1,3 cGP)

The method described in Example 1 for 1,3 cGP was followed by reacting 2-benzyloxy-1,3-propanediol with phenyl phosphorodichloridate (Aldrich). The intermediate benzylated product was pure on thin layer chromatography (ethyl acetate:hexane 3:2 $R_f$=0.58), with a melting point of 136° C. It was further hydrogenated as in Example 1 to remove selectively the benzyl residue. The obtained P-1,3 cGP, compound m, was pure on thin layer chromatography (as above) with $R_f$=0.15 and melting point of 116° C.

Example 4

Synthesis of 1,3 Cyclic Propanediol Phosphate (1,3 cPP)

1,3 cPP was prepared by reacting 1,3-propanediol (Aldrich) with an equimolar amount of phosphorus oxychloride and then purified as described by Buwalda et al., 1997. The product was isolated as the free acid (melting point: 99–100° C.).

$^{32}$P labeled 1,3 cPP (1,3 cP$^{32}$P) was prepared with $^{32}$POCl$_3$. The latter was obtained by introducing a trace of $H_3{}^{32}PO_4$ (Amersham) into an excess of POCl$_3$ in the cold (Neuhaus and Korkes, 1958). The reaction was then proceeded on a microscale and 1,3 cP$^{32}$P was isolated by co-crystallization with unlabelled 1,3 cPP.

Example 5

Synthesis of 1,2 Cyclic Propanediol Phosphate (1,2 cPP)

1,2 cPP was prepared by the same procedure as in Example 4 but using 1,2-propanediol (Aldrich). The compound was isolated as the Ba salt and was pure on paper chromatography (n-propanol:ammonia:water 6:3:1, $R_f=0.55$).

Example 6

Synthesis of Phenyl 1,3 Cyclic Propanediol Phosphate (P-1,3 cPP)

P-1,3 cPP was prepared by a method analogous to the procedure of Example 4, by reaction of 1,3-propanediol with an equimolar amount of phenyl phosphorodichloridate in dry pyridine. The product was crystallized twice from ethyl acetate-hexane and had a melting point of 72° C.

Example 7

Synthesis of Phenyl 1,2 Cyclic Glycerophosphate (P-1,2 cGP)

This novel compound was prepared as in Example 3 by reaction of 1-benzyloxy-2,3-propanediol with phenyl-$PO_2Cl_2$, followed by removal of the benzyl residue by selective hydrogenation. Crystallization was achieved from ethanol-acetone and the product had a melting point of 95° C.

Example 8

Synthesis of Phenyl 1,2 Cyclic Propanediol Phosphate (P-1,2 cPP)

This novel compound was prepared as in Example 6 by reaction of 1,2-propanediol with an equimolar amount of phenyl-$POCl_2$ in dry pyridine. Crystallization was achieved from ethyll acetate-hexane and the product had a melting point of 69° C.

Example 9

Synthesis of Cyclic Dihydroxyacetone Phosphate (cDHAP)

This novel compound was prepared by reaction of $POCl_3$ with dihydroxyacetone.

1.8 g (0.01M dimer or 0.02M monomer) Dihydroxyacetone dimer MW-180 dissolved in 20 ml fresh distilled methylene chloride.

3.07 g=1.87 ml (0.02M) Phosphoryl chloride (MW-153.5, d-1-645) in 4 ml $MeCl_2$ was slowly added to the solution at RT. The solution was refluxed for 15 h (the solution was black). Methylene chloride was evaporated and 100 ml 90% acetone/water was added to the solution. The reaction mixture was refluxed for 18 h. The black solution was treated with active carbon at RT and filtered. From the resulting slightly yellow solution was evaporated acetone and water and the very nice crystalline residue was dissolved in 10 ml acetone. 0.01 M $BaJ_2$ in 80 ml acetone was added to the solution and nice crystals of cyclic-dihydroxyacetone-phosphate barium salt started to precipitate. The precipitate was washed 3 times with small quantities of acetone and dried. The product was cleaned by dissolving it in small amounts of water and precipitating with acetone. The resulting produce is white crystalline powder and shows in paper chromatography (solvents mixture: n-Propanol:$NH_4H_2O$ 6:3:1) $R_f$-0.50.

Example 10

Synthesis of Phenyl Cyclic Dihydroxyacetone Phosphate (P-cDHAP)

This novel compound was prepared by reaction of phenyl-$PO_2Cl_2$ with dihydroxyacetone in dry pyridine. Upon removal of the solvent by vacuum, the residue was extracted twice with ethyl acetate. After evaporation of the ethyl acetate, an oily residue was obtained.

Example 11

Synthesis of Cyclic Oleyl Lysophosphatidic Acids (c-lysoPA)

These novel compounds were prepared by reaction of oleyl lysophosphatidic acid (Avanti Polar Lipids) with excess dicyclohexylcarbodiimide (DCC) in dimethyl sulfoxide. The product appeared as a oil.

Biological Section

Materials and Methods (i) Cells

Chinese hamster ovary (CHO) cells (Puck, 1985; Gottesman, 1987) and NIH-3T3 cells (NIH), were used in the following experiments. CHO cells were grown at 37° C. in a humidified 5% $CO_2$ atmosphere in 60×15 mm Petri dishes (Falcon) containing F12 medium supplemented with 10% fetal calf serum (FCS) and 2 mM glutamine. When reaching near confluence, the cells were placed under overnight starvation by replacing the medium to F12+2 mM glutamine with 0.1% FCS. The stimulation experiments were performed with cells which were under starvation for 12–18 hours.

NIH-3T3 cells were grown under similar conditions in 1640 Eagle medium at 10% bovine calf serum plus 2 mM glutamine.

(ii) Tyrosine Phosphorylation

The cyclic phosphates 1,3 cGP, 1,3 cPP, 1,2 cGP, 1,2 cPP, P-1,3 cGP and P-1,3 cPP and the controls αGP and βGP were dissolved in HBSS, or methanol to form stocks of 1 mM or 10 mM. They were diluted into the cell culture medium to a final concentration of up to 20 $\mu$M. At the assigned stimulation time (0.5–20 min.) the medium was aspirated under vacuum and the cells were washed 3 times with cold (4° C.) phosphate buffered saline (PBS). The cells were then freeze-thawed 3 times with liquid nitrogen in 0.5 ml of a lysis buffer of PBS containing 1 mM phenylmethylsulfonyl fluoride, a cocktail of protease inhibitors (aprotinin, leuproptin, pepstatin A, phenanthroline, benzamidine HCl each at a concentration of 10 $\mu$g/ml) and a cocktail of phosphatase inhibitors (80 mM β-glycerophosphate, 2 mM EGTA and 50 $\mu$M $Na_3VO_4$), and then scraped off. The lysate was then vortexed and centrifuged for 2 minutes at 12.000 g. The supernatant was collected for further determinations by gel electrophoresis. The protein concentration in each sample, as evaluated by the Bradford assay, was in the range of 1–1.5 mg/ml. Aliquots of 10 $\mu$g protein were applied onto 10% SDS-PAGE in a minigel set and resolved within 1 hour. The proteins were then transferred to nitrocellulose sheets for Western blotting. After blocking with a solution of 1% bovine serum albumine and 0.1% Tween 20 in PBS, the blots were incubated at 4° C. for 16 hours with polyclonal rabbit anti-phosphotyrosine antibodies (Zymed Laboratories, San Francisco, Calif.) or monoclonal anti-phosphotyrosine antibodies (Transduction Laboratories, Lexington Ky.) and then washed several times. Bound antibodies were detected by horseradish peroxidase-conjugated anti-rabbit antibodies (Transduction Laboratories, Lexington Ky.) after 2 hours incubation at room temperature, using the conventional ECL detection method. Control assays were carried out in the presence of 5 mM phosphotyrosine or without the phosphotyrosine antibodies. In both, the intensity of the bands was reduced to background level.

(iii) Threonine Phosphorylation

Blots were tested analogously for threonine phosphorylation using polyclonal rabbit anti-phosphothreonine antibodies (Zymed Laboratories, San Francisco, Calif.).

(iv) In-Gel Kinase Assay

Phosphorylated cell proteins were separated by SDS-PAGE using a gel that was copolymerized with MBP (0.5 mg/ml) and treated as described (Karunuguran et al., *EMBO J.* 15:254–264, 1996). After electrophoresis, the gel was fixed with isopropanol and denatured using 6M Urea. Renaturation was achieved by gradual removal of the excess of urea followed by extensive washings in a renaturing buffer (16 h, 4° C.) and in a buffer containing 20 nM HEPES pH 7.6, and 20 mM $MgCl_2$ (30 min, 30° C.). The gel was then subjected to phosphorylation in a buffer containing 20 mM HEPES pH 7.6, 20 mM $MgCl_2$, 2 mM DTT, 20 μM ATP and 100 mCi $[y^{32}P]$-ATP (30° C. for 120 min). Finally the gel was extensively washed, dried, and subjected to autoradiography.

(v) Immunoprecipitation kinase assays. Raf-1 Activity was determined by immunoprecipitation with anti-Raf-1 C terminus antibodies (Santa Cruz Biotech, CA) using recombinant MEK1 as a substrate as previously described (Seger, 1994). Mitogen-activated protein kinase (MAPK) activity was determined by immunoprecipitation with anti-ERK2 C terminus antibodies (Santa Cruz Biotech, CA) using MBP as a substrate (Seger, 1994). Jun N-terminal kinase (JNK) activity was determined by purifying the JNK on a GST-Jun (1-97) column followed by phosphorylation (Hibi, 1993). Results

Example 12

Tyrosine Phosphorylation in CHO Cells by 6-Membered Ring Cyclic Phosphates Detected with Polyclonal Antibodies CHO cells were contacted for 1 min. at 37° C. with 1 μM of αGP, βGP, 1,3cGP(E), P-1,3-cPP and the level of tyrosine phosphorylated proteins in the cells was then determined by using polyclonal anti phosphotyrosine antibodies as explained above.

As seen in FIG. 1, augmented tyrosine phosphorylation was induced by all of the above cyclic phosphates in a series of proteins as seen in several major bands having μM of about 35 kD, 45 kD, 60–70 kD and about 120 kD.

Example 13

Tyrosine Phosphorylation in CHO Cells by 6-Membered Ring Cyclic Phosphates Detected with Monoclonal Antibodies CHO cells were contacted for 1 min. with the same linear and cyclo glycerophosphates described in Example 12 above under the same conditions. Determination of the level of tyrosine phosphorylated proteins in the cells was determined using a monoclonal anti phosphotyrosine antibody of the kit described above. Using this antibody, the detected tyrosine phosphorylation was in bands having a molecular weight of about 35 kD and of about 45 kD (results not shown).

Example 14

Tyrosine Phosphorylation in CHO Cells by 1,3,-cPP at Various Concentrations

CHO cells were incubated for a period of 1 min., 3 mins., 5 mins. or 10 mins. at 37° C. with 1 μM or 2 μM of 1,3-cPP. The level of tyrosine phosphorylated proteins in the cells was determined using monoclonal anti phosphotyrosine antibodies.

Figure 2:
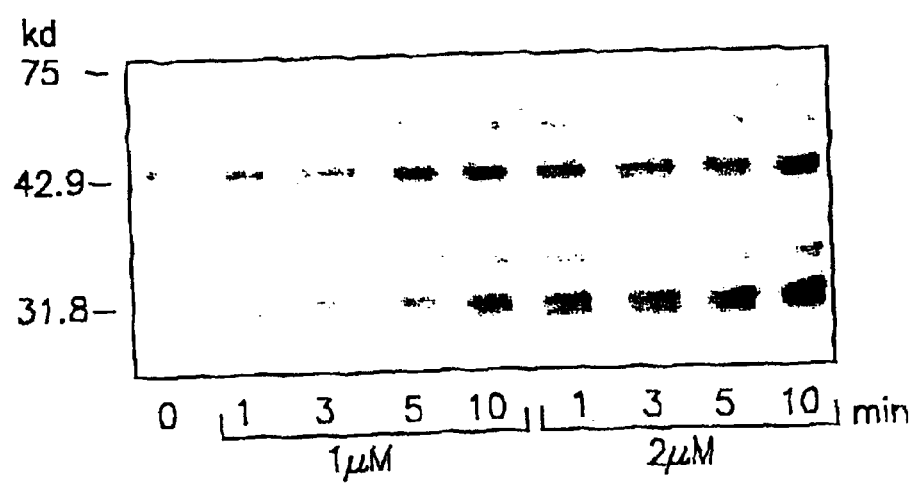
FIG. 2 shows the level of tyrosine phosphorylated proteins in CHO cells after 1 min pulsing at 37° C. with 1 $\mu$M and 2 $\mu$M 1,3 cPP. Detection with monoclonal anti-phosphotyrosine antibodies.

As seen in FIG. 2, phosphorylation was most markedly seen in the band(s) having a molecular weight of about 35 kD and about 45 kD.

Example 15

Tyrosine Phosphorylation in NIH 3T3 cells by 6-Membered Ring Cyclic Phosphates as Detected by Polyclonal Antibodies The level of tyrosine phosphorylated proteins in NIH 3T3 cells was determined after their incubation for 1 min. at 37° C. with αGP, βGP, 1,3cGP(E), P-1-3 cPP. The level of tyrosine phosphorylated proteins in the cells was determined using polyclonal anti phosphotyrosine antibodies.

Augmented tyrosine phosphorylation was induced in the cells by all the above cyclic phosphates (results not shown).

Example 16

Tyrosine Phosphorylation in NIH 3T3 Cells by 6-Membered Ring Cyclic Phosphates as Detected by Monoclonal Antibodies The level of tyrosine phosphorylated proteins in NIH 3T3 cells was determined as described above after their incubation for either 1 min. or 5 mins. at 37° C. with 0.5 μM, 1 μM, 2 μM or 4 μM of 1,3-PP. The level of tyrosine phosphorylated proteins was determined using monoclonal anti phosphotyrosine antibodies as described above.

Figure 3:
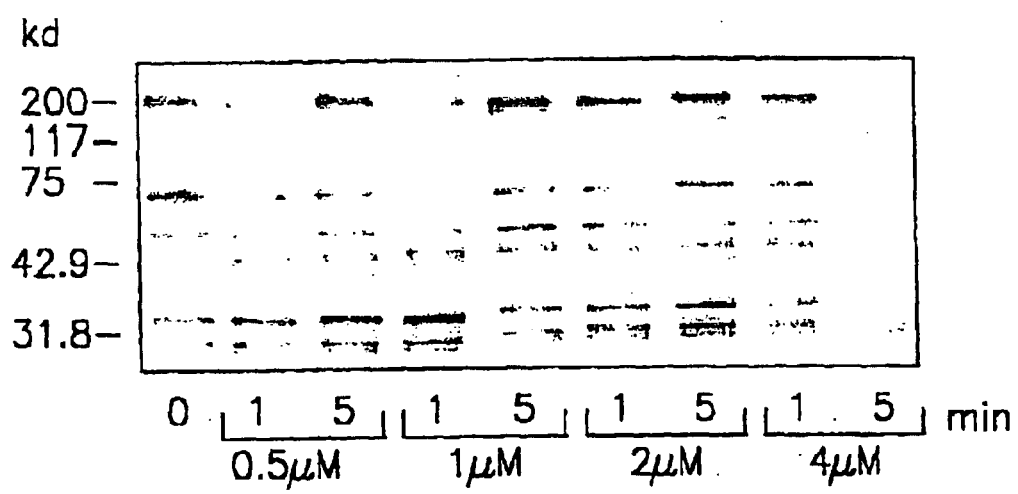
FIG. 3 shows the level of tyrosine phosphorylated proteins in NIH 3T3 cells after 1 min pulsing at 37° C. with 1,3 cPP. Detection with monoclonal anti-phosphotyrosine antibodies.

As seen in FIG. 3, augmented tyrosine phosphorylation was seen in the cells similar to that seen in the cells of Example 14 above.

Example 17

Tyrosine Phosphorylation in NIH 3T3 cells by 5-Membered Ring Cyclic Phosphates

Induction of tyrosine phosphorylation in cells by 5-membered ring cyclic phosphate (see Appendix 1) was carried out as described in Example 12 above.

The pattern of tyrosine phosphorylation was similar to that obtained by incubation of the cells with the 6-membered ring cyclic phosphates but at a relatively higher concentration and at longer incubation times (results not shown).

Example 18

Kinetics of Tyrosine Phosphorylation in CHO Cells

Figure 4:
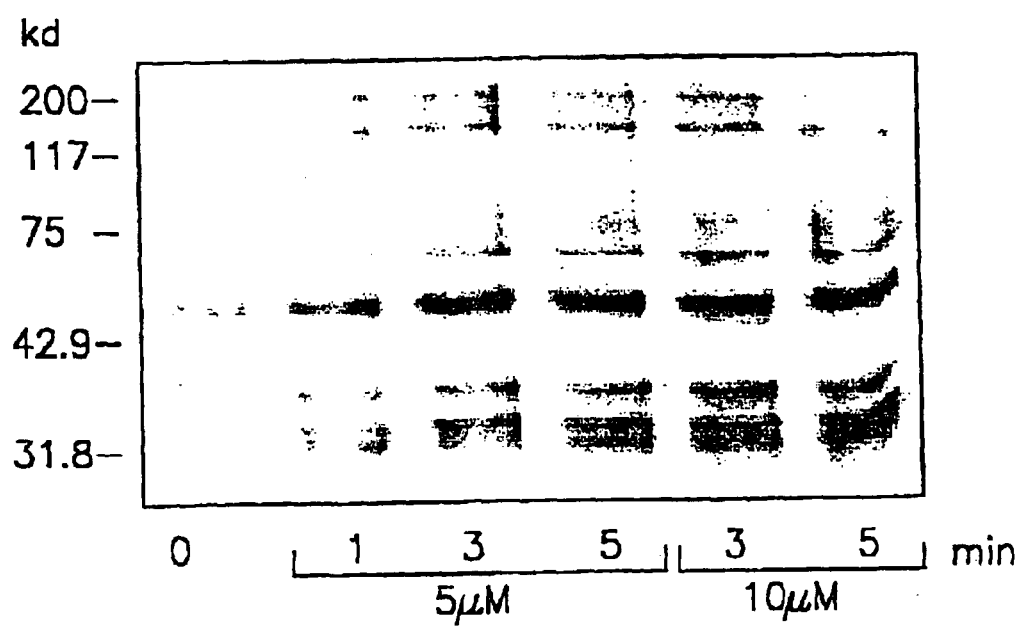
FIG. 4 shows the time course of tyrosine phosphorylation in proteins of CHO cells pulsed with 5 $\mu$M and 10 $\mu$M 1,2 cPP for a period of 1 min., 3 mins. or 5 mins. Detection with monoclonal anti-phophotyrosine antibodies.

The kinetics of tyrosine phosphorylation in proteins of CHO cells incubated with either 5 μM or 10 μM of 1,2-cPP at 37° C. for a period of 1 min, 3 mins. or 5 mins. was determined as described above using monoclonal anti phosphotyrosine antibodies. As seen in FIG. 4, enhanced tyrosine phosphorylation was detected at bands having μM of about 35 kD, 60–70 kD, 120 kD and an additional band of about 38 kD. Similar results were obtained using the deoxy analog of 1,2-cPP (results not shown).

Example 19

Induced Tyrosine Phosphorylation in Cells as Detected by in Situ $^{32}P$ Labeling To further verify the induced tyrosine phosphorylation shown in the above examples, in situ $^{32}P$ labeling of CHO cells was carried out under a pulse of cyclic phosphate as described above. $10^7$CHO cells/per 1 ml medium were pulsed with 1 mCi of $^{32}PO_4^{-3}$ for 12 hours and then activated for 2 mins. with 2 μM of 1,3-cGP(E) or 2 μM of 1,3-cPP. As control, the same cells following the 12 hour pulsing were not contacted with the cyclic cGPs. Massive $^{32}$P protein labeling was observed in both the cells which were incubated with the cyclic GMPs as well as with one set that were not.

Figure 5:
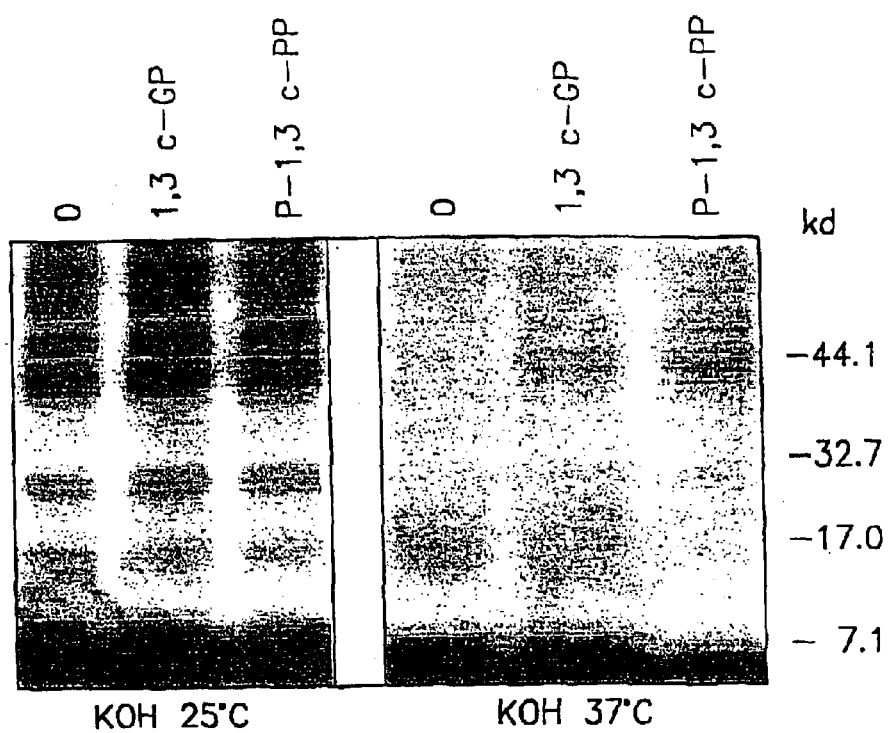
FIG. 5 shows the $^{32}$P labelled proteins of CHO cells after 2 min pulsing with 2 $\mu$M 1,3 cGP (E) or 1,3 cPP followed by gel electrophoresis and in-gel treatment with 1 M KOH.

However, as seen in FIG. 5, following treatment of the gel with 1M of KOH for 2½ hours at 25° C. or 37° C. (which selectively hydrolyzes the phosphoserine and phosphothreonine residues (Kozma et al., *J. Methods Enz.*, 201;28–43, 1991), two major $^{32}$P bands of phosphorylated tyrosine at molecular weights of about 35 kD and 45 kD emerged in the treated samples. These bands could be correlated with kinase activity (see Example 20 below).

Example 20

Detection of Phosphorylated Kinases by In-Gel Kinase Assay

The in-gel kinase assay in the presence of MBP was applied as described in Materials and Methods above to detect stimulation of protein kinases by the cyclic phosphates. CHO cells were treated either with medium (0 control), or with 2 μM, α GP or β GP for 2 minutes, 2 μM 1,3-GP (E) for 2 and 5 minutes and 2 M 1,3-cPP for 2 minutes after which the cells were lysed and analyzed.

Figure 6:
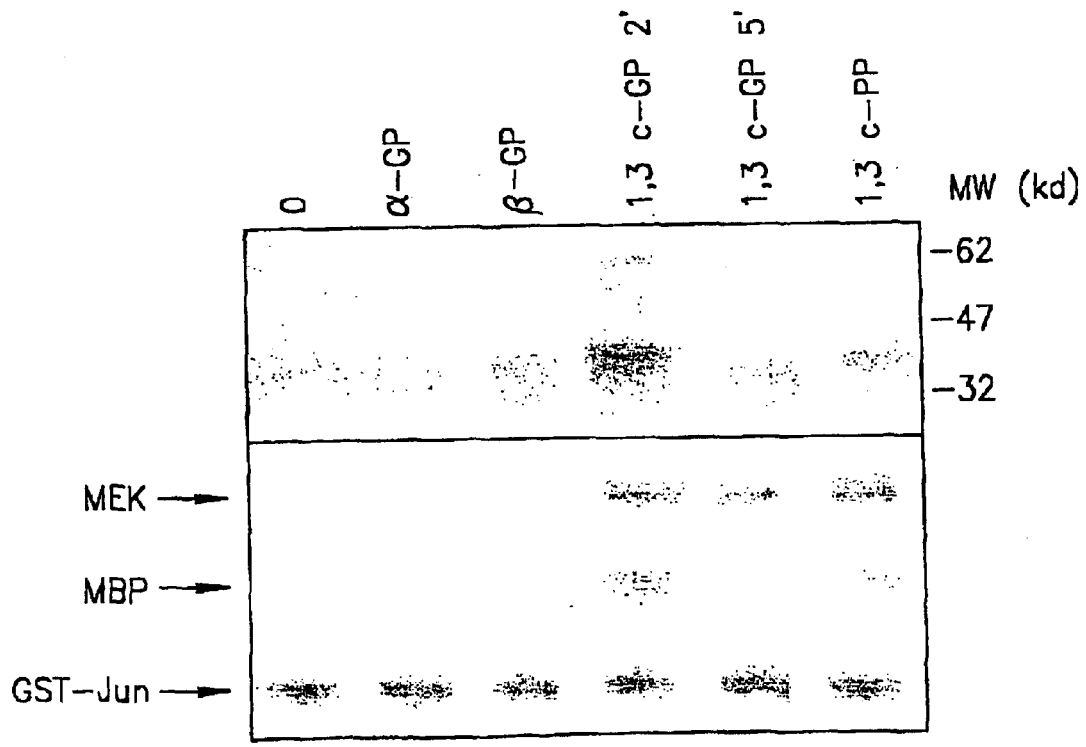
FIG. 6 shows the in-gel assay for kinase identification of proteins from CHO cells phosphorylated by 2 $\mu$M 1,3 GP or 1,3 cPP in comparison to 2 $\mu$M αGP or βGP (control). In-gel identification of Raf-1, MAPK and Jun kinase in the phosphorylated proteins is shown in the lower panel.

As seen in FIG. 6, at least three MBP phosphorylated kinases could be detected by this method. Their apparent molecular weights were around MW of 35–40, 55 and 62 kD. The 35–40 kD protein kinase which was activated by 1,3-cGP (E) could be assigned to the P42 MAPK (ERK 2). In addition, cells were treated as described above and then subjected to Raf-1, MAPK and IP kinase assays and these are presented in the first and second rows of FIG. 6. In parallel, JNK assay was performed (third row, JST-Jun substrate). The results strongly suggest that the Raf1/MAPK cascade is activated up to approximately 5 fold by 1,3-cGP (E), whereas the JNK pathway seems to be unaffected.

Example 21

Augmentation of Threonine Phosphorylation by 6-Membered Ring Cyclic Phosphates

Figure 7:
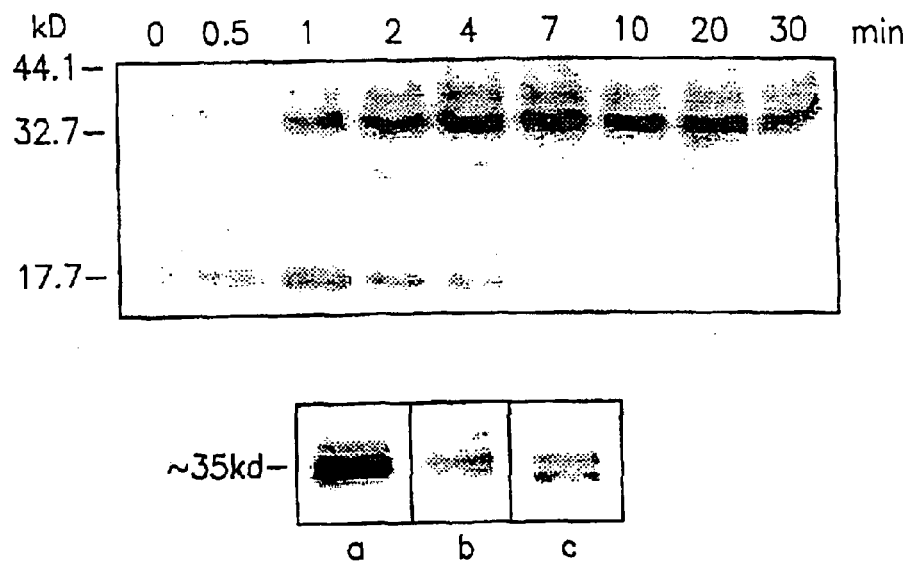
FIG. 7 shows the time profile of threonine phosphorylation in CHO cells induced by 4 $\mu$M 1,3 cGP (E) at 25° C. Abolishment of detection of threonine phosphorylation (a) by the presence 5 mM phosphoserine (b) or 5 mM phosphothreonine (c) is also shown.

In both the CHO and the NIH-3T3 cells a high level of constitutive phosphoserine containing proteins did not permit an unequivocal detection of changes induced by the tested cyclic phosphates. However, as seen in FIG. 7, a marked augmentation in threonine phosphorylation induced by the six membered ring cyclic phosphates could be clearly detected in three specific proteins (18 kD, 35 kD, 38 kD). As shown, at 25° C., the bands at molecular weight of about 35 kD and about 38 kD reached a maximum phosphorylation at around 7 mins. which was slowly diminished while the band at about 18 kD displayed a much sharper phosphorylation-dephosphorylation profile. The presence of 5 mM phosphothreonine in the antibody binding assay reduced the intensity of the 35 KD band to the control level.

Example 22

Stability of the Cyclic Glycerophosphates

In principle, cyclic phosphates can be hydrolyzed to the respective linear forms (e.g. α-GP) either spontaneously or through putative phosphodiesterases. These possibilities were tested with the 4 cyclic phosphates (1,2 cGP, 1,3 cGP, 1,2 cPP and 1,3 cPPP (see Appendix A) in either aqueous solution or in cell lysates of CHO or NIH-3T3 cells (see Materials and Methods). 10 mg/ml cyclic phosphate in 1 ml of either PBS or PBS mixed with cell lysate (0.1 mg/ml protein) and incubated at 37° for up to 24 hours. Samples were tested at different times by thin layer chromatography on Silica gel 60 with n-propanol, concentrated ammonia, $H_2O$ (6:3:1 v/v/v). The Rr values for all 4 cyclic phosphates was in the range of 0.45–0.55 while α-GP and β-GP had $R_f$=0.14–0.16. This distinct difference allowed the qualitative detection of hydrolysis of the cyclic phosphate. No hydrolysis of the tested cyclic phosphates either in PBS or by the cell lysate was detected. Furthermore, aqueous solutions of all the 6 cyclic phosphates were found to be stable for at least several days at room temperature and for months below 0° C.

Example 23

Inhibition of Phosphatase and Phosphodiesterase Activity of Cell Lysates by Cyclic Phosphates Inhibition of phosphatase activity of cell lysate by cyclic phosphates was assayed in 1.0 ml of 50 mM Tris-HCl buffer, pH 7.4, containing 50 mM p-nitrophenyl phosphate, PNPP, as a substrate. Reaction was initiated by the addition of crude cell lysate (100 μg/ml final protein concentration) and terminated after 90 minutes at 37° C. by an addition of 50 μl of 1M NaOH. The absorbance of the released p-nitrophenol was measured at 405 min. Assays were conducted under the same conditions as above in the presence of 50 μM cyclic phosphate. The enzyme activity in the absence of inhibitor was taken as 100% activity.

Only 1,3 cGP(E) obtained from PLase C cleavage of PG (see Materials and Methods) displayed a limited inhibition of the lysate phosphatases.

Synthetic 1,3 cGP, unlike the enzymatic product, displayed only approximately 10% inhibition at 50 μM concentration. Similarly, 50 μM 1,3 cPP displayed 15–20% inhibitory capacity. All other cyclic phosphates, as well as αGP and βGP at a concentration of 50 μM induced less than 5% inhibition of the cell lysate phosphatase activity.

In a series of analogous experiments phosphodiesterase activity of the cell lysates in the presence and absence of the cyclic phosphates was tested. In these experiments bis p-nitrophenyl phosphodiester was used as a substrate. No significant effect of any of the cyclic phosphates on the cell lysate phosphodiesterase activity was observed (not shown).

Example 24

Uptake of $^{32}$P Labeled 1,3-cPP by CHO Cells

Figure 8:
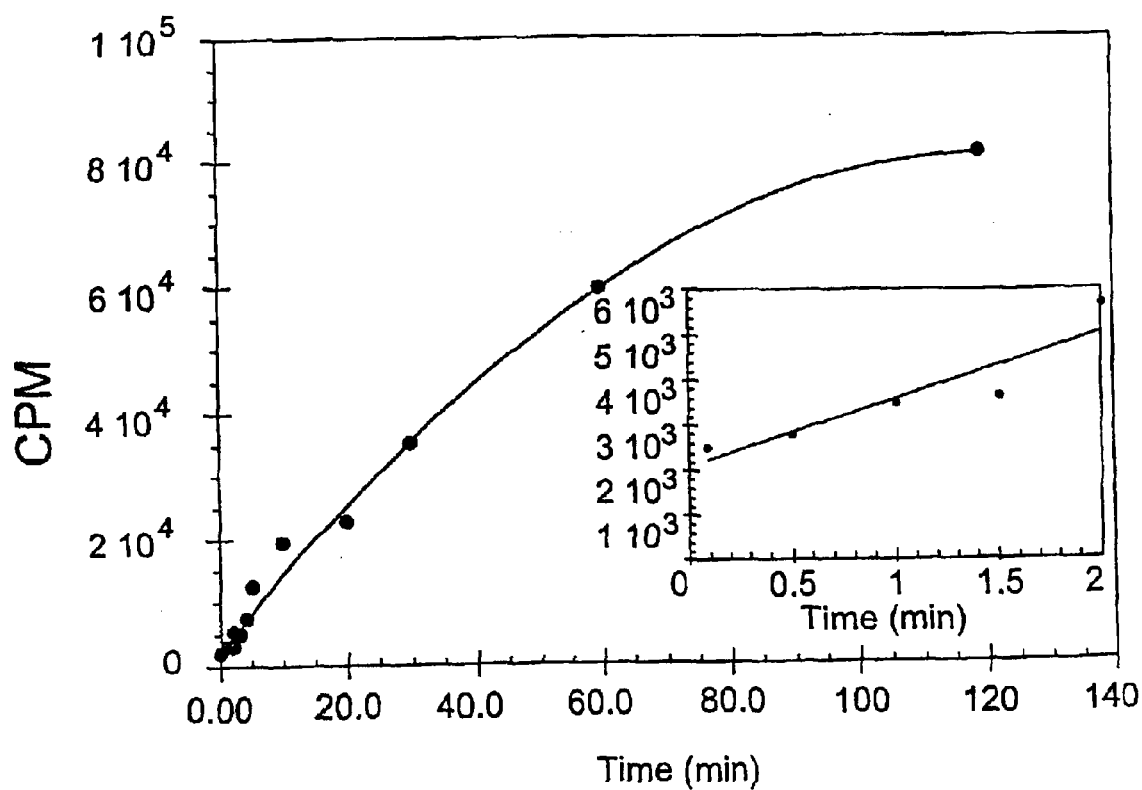
FIG. 8 shows the uptake profile of 1,3 cP$^2$P (10 $\mu$M) by CHO cells. The inserts presents the magnified profile for short incubation times.

Binding and incorporation assays were carried out with $^{32}$P labeled 1,3-cPP (1,3-cP$^{32}$P), the only one of the cyclic phosphates which could be synthesized in a relatively high specific activity (see Materials and Methods). When contacted with CHO cells there was a rapid apparent binding of 1,3-cP$^{32}$P followed by a continuous uptake which leveled off after approximately 2 hours of incubation. A typical profile of binding and incorporation of 1,3-cP$^{32}$P is shown in FIG. 8. In this experiment a triplicate of 1 ml samples each containing $2\times10^6$ CHO cells and 10 μM 1,3-cP$^{32}$P (approximate specific activity 10 μci per μmole) were incubated in the starvation medium for different times. After 2 washings with PBS the cells were disintegrated in 1 M NaOH and radioactivity was scored with a β counter. The insert presents the magnified uptake profile for short incubations (up to 2 minutes) where the intercept (0 time incubation) corresponded to approximately $3 \times 10^6$ molecules per cell, while at equilibrium (above 2 hours incubation) incorporation corresponded to approximately $2 \times 10^8$ molecules per cell. This profile remained essentially unaltered in competition experiments where 1,3-$cP^{32}P$ was mixed with increasing amounts of unlabeled 1,3-cPP or 1,3-cGP, indicating that the apparent binding extrapolated for 0 time incubation and the following incorporation proceeded through non-specific binding.

Without being limited to theory this mode of uptake may be explained by a mechanism by which 1,3-cPP and probably the other cyclic phosphates as well, first incorporate rapidly and non specifically into the cell plasma membrane (probably the lipid layer), where it reaches a steady-state concentration after a few seconds. Through this compartment the cyclic phosphate partitions further with the cytosol to reach an equilibrium with the external medium after approximately 2 hours. This passive partitioning mechanism is further supported by the estimated concentration of the intracellular concentration of 1,3 $cP^{32}P$ at the equilibrium which is in the micromolar range, i.e. the range of the external 1,3 $cP^{32}P$ concentration. It is of interest to note that after 5 minutes of incubation, when tyrosine phosphorylation is maximal (see for example FIG. 3) the intracellular concentration of the cyclic phosphate is in the order of $10^7$–$10^8$ molecules per cell.

Example 25

Intracellular Binding of Cyclic Phosphates by CHO Cells

Figure 9:
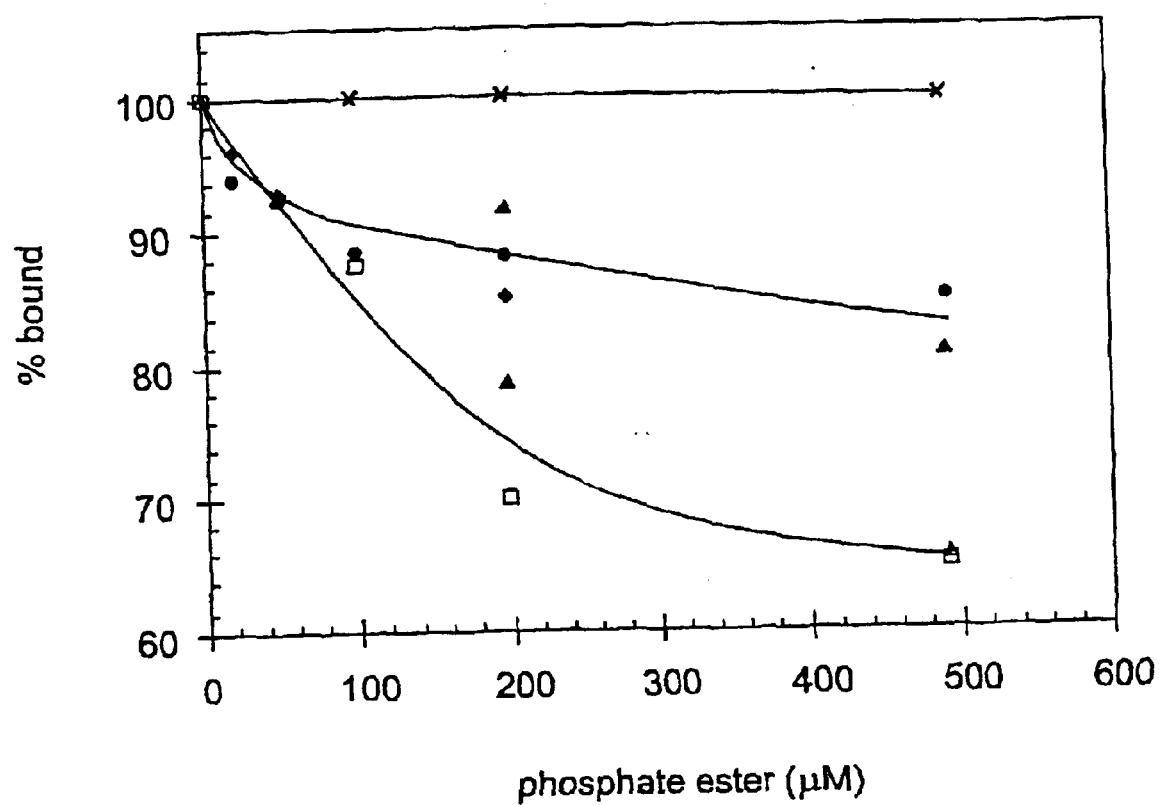
FIG. 9 shows the displacement profiles of 1,3 cP$^{32}$P in perforated CHO cells by αGP (x-x), unlabelled 1,3 cPP (filled symbols, 3 separate experiments) and 1,3 cGP (E) (open symbols, 2 separate experiments).

In an attempt to characterize the intracellular binding of the cyclic phosphates, perforated CHO cells ($2 \times 10^6$ in 1 ml of 1:1 v/v ethanol in PBS) were incubated for 5 minutes at 4° C. with 20 μM 1,3-$cP^{32}P$ (see above) and increasing amounts of either αGP, unlabeled 1,3-cPP or 1,3-cGP. Radioactivity was scored after 2 washings with PBS at 4° C. as above. As shown in FIG. 9, competition with unlabeled 1,3-cPP is displayed indicating specific binding. Similarly, clear binding competition was also observed with 1,3-cGP while αGP was ineffective. In this set of experiments the number of displaceable (i.e. specifically bound) ligands was estimated to be in the range of $10^7$–$10^8$ per cell. Such a high number suggests low affinity ubiquitous targets, rather than specific receptors.

Example 26

Effect of Cyclic Phosphates on Differentiation of Human Breast Cancer Cells

The effect of the cyclic phosphates on the differentiation of human breast cancer cells was determined by detecting cell marker characteristics connected with differentiation. Highly undifferentiated breast cancer cells are characterized by low level of progesterone and estrogen receptors. Patients with such tumor have a poor prognosis. Partially differentiated breast cancer cells contain a significantly higher level of these receptors. Two available cell lines (established by Prof. Y. Kedar, Tel Aviv University, Tel Aviv, Israel) are used, which are of low and high estrogen and progesterone receptors, respectively. Cells are incubated in tissue culture medium with or without 1–10 μM cyclic phosphate or αGP (as a control). Change in receptor level in these cells is monitored by conventional Western Blot analysis using known anti estrogen and anti progesterone receptor monoclonal antibodies.

Example 27

Effect of Cyclic Phosphates on Differentiation of Human T-Leukemia Cell Lines

High virulent human T-leukemia cell lines (e.g. Jurkat cells) are cultured with various cyclic phosphates as above. The effect of the cyclic phosphates in these cells is monitored by the emergence of differentiation markers on the cell surface (e.g. CD3). Their quantity is determined by conventional FACS analysis using fluorescent antibodies.

Example 28

Effect of 1,3,cPP in Combination with Insulin on Phosphorylation of Cells Expressing the Insulin Receptor Binding of insulin to its receptor on the cell surface results in rapid tyrosine phosphorylation on the 117 kD and 200 kD receptor proteins. This is the initial event in the overt functions of insulin (e.g. glucose uptake).

CHO-T cells expressing the insulin receptor (obtained from Prof. Y. Zick, The Weizmann Institute, Rehovot, Israel) were divided into four groups, each incubated for 20 mins. with one of the following:

Group 1: 1 nM insulin which results in maximal phosphorylation of the receptors.

Group 2: 0.1 nM insulin resulting in partial phosphorylation of the receptors, in situation analogous to refractory response such as occurs in IDDM Type 2.

Group 3: 0.1 nM insulin and 0.1 μM 1,3, cPP; and

Group 4: 0.1 μM 1,3, cPP only.

Tyrosine phosphorylation was determined using anti-phosphotyrosine antibody (as described above). Phosphorylation was determined in the two protein bands of the insulin receptor having a molecular weight of 117 kD (FIG. 10A) and 200 kD (FIG. 10B).

Figure 10:
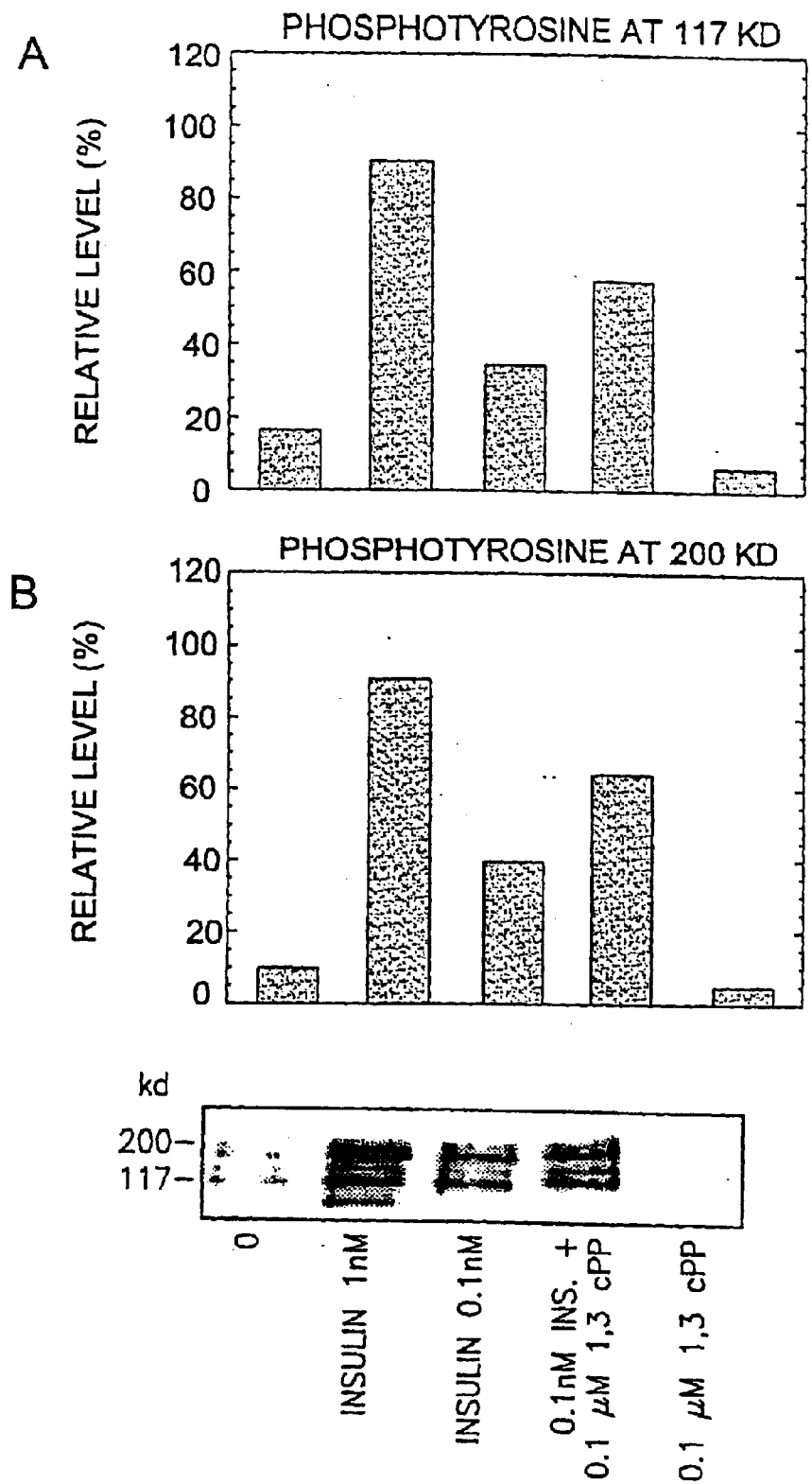
FIG. 10 is a schematic representation showing the relative level of phosphorylation of insulin receptors on CHO-T cells following their incubation with insulin (1 nM or 0.1 nM), 1,3, cPP (0.1 $\mu$M) or a combination of both.

As seen in FIG. 10, incubation of the insulin receptor expressing cells with a combination of insulin (0.1 nM) and 1,3 cPP almost doubled the phosphorylation obtained in the cells incubated with insulin only. Thus, the tested GC shows synergistic activity with insulin.

Example 29

Tyrosine Phosphorylation of Erb-b2 Receptor on CHO Cells by Cyclic Glycerophosphate CHO cells expressing the human growth factor receptor (HGF) Erb-b2 (prepared by Y. Yarden, Weizmann Institute, Rehovot, Israel) are divided into the following four groups:

Group 1: Cells incubated for about 20 mins. with HGF at a concentration resulting in maximal phosphorylation of the HGF receptor, Group 2: Cells incubated with concentrations of HGF resulting in partial phosphorylation of the receptor, Group 3: Cells incubated with a combination of HGF in the lower concentration and the tested cyclic glycerophosphate; and Group 4: Cells incubated with the tested glycerophosphate alone.

The percent of tyrosine phosphorylation of Erb B2 is monitored using known antibodies as described above.

Example 30

Augmentation of Estrogen Receptor (ER) Receptor Expression in Human $ER^{mod}$ $T_{47}D$ Cells Tumor cells were incubated for 7 days in the absence or presence of 1 μM of 1,3 cGP. On each of the noted days, cells were harvested by trypsinization, washed and fixed by dryng in air. The preparations were then peroxidased and protein blocked. Following this, the cells were labeled with first antibody (mouse-anti-human ER) for 30 mins. at room temperature (RT). After washing, cells were incubated with biotinylated second antibody for 10 min at RT. After washing, the cells were incubated with streptavidin conjugated to horse radish peroxidase and color reaction with the DAB reagent was performed. Background staining was done with hematoxylin (mayer) and the fixation process was completed with water, alcohol and finally xylene immersions. The slides were covered, sealed and examined by a pathologist in a blind fashion. Expression of the ER was scored on a scale of 0 to 4 pulses, where 4 pulses is the highest score.

Figure 11:
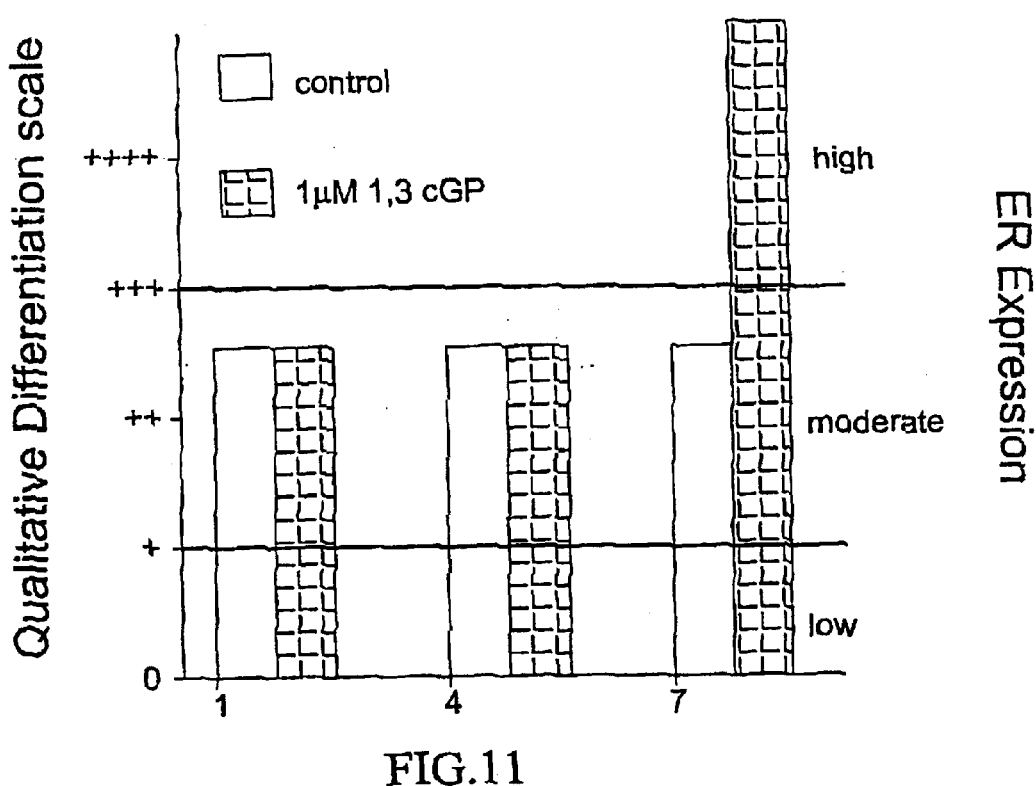
FIG. 11 is a schematic representation showing the level of expression of the estrogen receptor (ER) in human ER$^{mod}$ T$_{47}$D cells incubated with the cyclic phosphate 1,3 cGP or in the culture medium as control. The results are shown 1, 4 and 7 days after beginning of incubation.

As seen in FIG. 11, following 7 days of incubation of the cells with 1,3, cGP, the level of expression of ER on the cells was significantly higher than the level of expression of ER in cells incubated in growth medium alone. Thus, incubation of these malignant cells with this 1,3 cGP results in their differentiation.

Example 31

Inhibition of Proliferation of $T_{47}D$ Human Breast Cancer Cells by 1,3-cPP In this experiment, $8 \times 10^4$ $T_{47}D$ (clone 11) human breast cancer cells were plated in sets of 6 in 96 well microtiter plates and titrated concentrations (1–50 μM final concentrations) of 1,3-cPP salt in complete medium were added to the cultures at the beginning of the experiment only in a total volume of 200 μl per well. Plates were incubated at 37° C. over the course of 5 days, where 1 plate was pulsed with $^3$H-thymidine (Sigma) overnight each day and subsequently frozen. All the plates were harvested together (Packard Micromate 196 Harvester, Merriden, Conn.) and scored on a 96 well plate reader (Packard Matrix 96, Merriden, Conn.).

Figure 12:
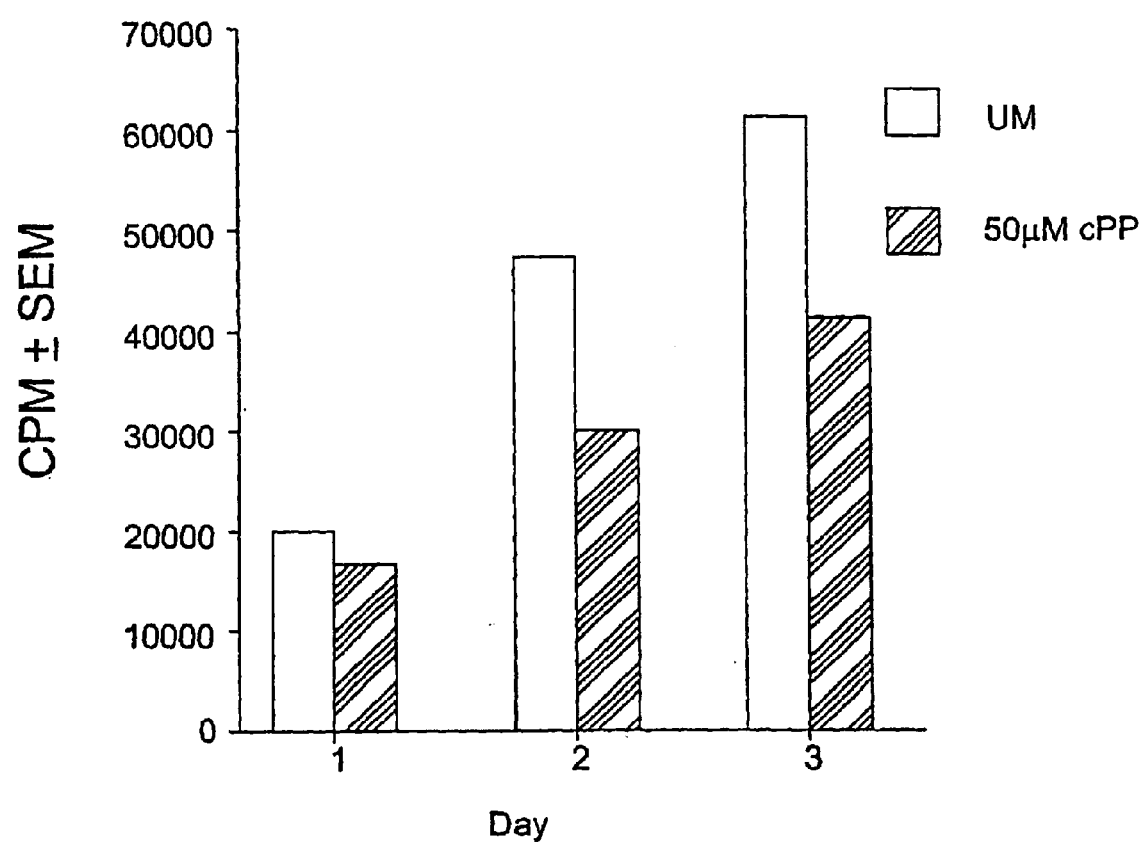
FIG. 12 is a schematic representation showing the level of proliferation of T$_{47}$D human breast cancer cells grown in vitro either with growth medium or with a final concentration of 50 μM of 1,3-cPP salt. The effect on proliferation is shown on days 1, 2 and 3 of the culture.

As seen in FIG. 12, incubation of the $T_{47}D$ cells with 1,3,cPP at a concentration of 50 μM resulted in significant inhibition of their proliferation as compared with the proliferation of the cells which were grown in growth medium only. The effect was observed after 1, 2 and 3 days of incubation (P values were 0.0370, 0.0192, and 0.0238 on days 1–3 respectively).

Example 32

Induction of Differentiation of K562 Leukemia Cells by 1,3, cPP

K562 leukemia cells are able to differentiate to the erythroid lineage. Such differentiation is characterized by the cells' ability to synthesize hemoglobin. Sodium butyrate is a known differentiation agent of such leukemia cells.

In this example, the ability of 1,3 cPP, α-GP and sodium butyrate alone and n combination to cause differentiation of K562 cells was evaluated using the known benzidine assay.

K562 cells were incubated for a period of 4 days with the following:

(a) growth medium (control);

(b) 10 μM of 1,3 cPP;

(c) 10 M of α-GP;

(d) 1.5 mM of sodium butyrate;

(e) a combination of sodium butyrate and 1,3 cPP; and (f) sodium butyrate and α-GP.

Figure 13:
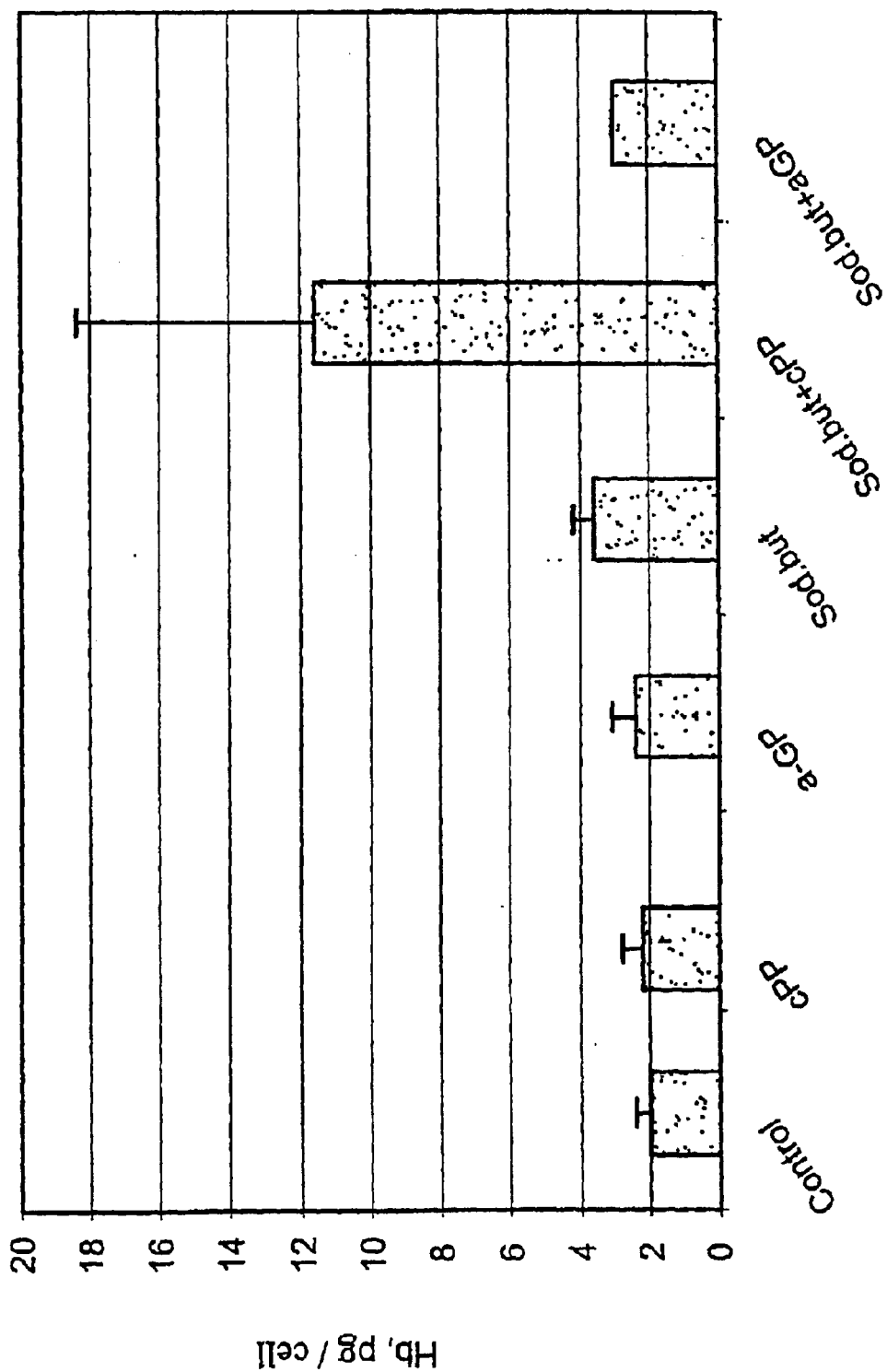
FIG. 13 is a schematic representation showing the amount of hemoglobin production in K562 leukemia cells following their incubation for four days with growth medium (control), 1,3 cPP, α-GP, a differentiation-inducing agent sodium butyrate and combinations thereof

As seen in FIG. 13, following a 4 day period of treatment, the synthesis of hemoglobin by the K562 cells which were incubated with a combination of sodium butyrate and 1,3 cPP was 3-fold greater than the level of hemoglobin synthesized by cells incubated with the differentiation inducing agent sodium butyrate alone. Thus, 1,3 cPP in combination with sodium butyrate caused significant differentiation of K562 leukemia cells to the erythroid lineage.

APPENDIX A

| | Formula | Abbreviation |
|---|---|---|
| I | (structure) | 1,3 cGP |
| II | $HO-CH_2-CH-CH_2$ (structure) | 1,2 cGP |
| III | $RC-CH_2-CH-CH_2$ (structure) | cyclic lysophosphatidic acid, c-lysoPA |
| IV | (structure) | P-1,3 cGP |
| V | $HO-CH_2-CH-CH_2$ (structure) | P-1,2 cGP |
| VI | (structure) | 1,3 cPP |

APPENDIX A-continued

| Formula | | Abbreviation |
|---|---|---|
| VII | CH₃—CH—CH2 with cyclic O-P(=O)-O, O⁻ | 1,2 cPP |
| VIII | CH₂-CH₂-CH₂ cyclic with O-P(=O)-O, Oφ | P-1,3 cPP |
| IX | CH₃—CH—CH₂ cyclic with O-P(=O)-O, Oφ | P-1,2, cPP |
| X | O=C with CH₂-CH₂ cyclic O-P(=O)-O, O⁻ | cDHAP |
| XI | O=C with CH₂-CH₂ cyclic O-P(=O)-O, Oφ | P-cDHAP |

What is claimed is:

1. A pharmaceutical composition comprising a pharmaceutically acceptable carrier and, as an active ingredient, a compound of the general formula I:

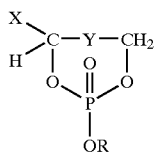

(I)

wherein

Y is —(CH₂)$_m$—, —CH(OH)— or —C(=O)—, and m is 1–3;

X is H, alkyl, —CH₂OH—, CH₂Oacyl or —CH₂acyl; and

R is H, a cation, alkyl or optionally substituted aryl; provided that:

Said compound is not one of (i) Phenyl 1,3-cyclic propanediol phosphate,
(ii) Cyclic dihydroxyacetone phosphate,
(iii) 1,3,-cyclic propanediol phosphate
(iv) 1,3-cyclic glycerophosphate.

2. A pharmaceutical composition according to claim 1, wherein said alkyl groups have 1–24 carbon atoms, said acyl groups are aliphatic saturated or unsaturated $C_1$–$C_{24}$ acyl groups and said aryl group is a carbocyclic aryl group optionally substituted by $C_1$–$C_4$ alkyl, halogen and/or hydroxy.

3. A pharmaceutical composition according to claim 2, wherein said acyl groups are derived from natural fatty acids.

4. A pharmaceutical composition according to claim 3, wherein said acyl group is (1) a saturated aliphatic acyl group selected from the group consisting of acetyl, butyryl, caproyl, octanoyl, decanoyl, lauroyl, myristyl, palmitoyl and stearoyl, or (2) an unsaturated aliphatic acyl group selected from the group consisting of palmitoleyl, oleyl, linoleyl, and ricinoleyl.

5. A pharmaceutical composition according to any one of claims 1–4, wherein said aryl group is phenyl.

6. A pharmaceutical composition according to claim 1, comprising cyclic oleyl lysophosphatidic acid.

7. A pharmaceutical composition according to claim 1, comprising phenyl 1,3-cyclic glycerophosphate.

8. A pharmaceutical composition according to claim 1, comprising phenyl cyclic dihydroxyacetone phosphate.

9. A pharmaceutical composition for inducing phosphorylation in intracellular proteins of target cells comprising a pharmaceutically acceptable carrier and, as an active ingredient, a compound of general Formula I of claim 1.

10. A pharmaceutical composition comprising a pharmaceutically acceptable carrier and, as an active ingredient, a compound of the general Formula I of claim 1 capable of promoting cell differentiation in target cells.

11. A pharmaceutical composition for the treatment of malignant diseases and disorders selected from the group consisting of blood malignancy, prostate cancer and breast cancer, comprising a pharmaceutically acceptable carrier and, as an active ingredient, a compound of the general Formula I of claim 1 wherein Y is —(CH₂)$_m$—, —CH(OH)— or —C(=O)—, and m is 1–3;

X is H, alkyl, —CH₂OH—, CH₂Oacyl or —CH₂acyl; and

R is H, a cation, alkyl or optionally substituted aryl.

12. A pharmaceutical composition according to claim 11, wherein said malignant disorder is a blood malignancy.

13. A pharmaceutical composition according to claim 12, wherein said blood malignancy is leukemia.

14. A pharmaceutical composition according to claim 11, wherein said malignancy is breast cancer.

15. A pharmaceutical composition comprising a pharmaceutically acceptable carrier and, as an active ingredient, a compound as defined in claim 1, capable of induction of insulin, human growth hormone or epidermal growth factor signaling.

16. A pharmaceutical composition comprising a pharmaceutically acceptable carrier and, as an active ingredient, a compound of Formula I as defined in claim 1, for capable of induction of hormone-like signaling wherein said hormone is selected from the group consisting of insulin, human growth hormone, and epidermal growth factor.

17. A pharmaceutical composition according to claim 15 or 16, wherein said hormone is insulin and the composition is for the treatment of non-insulin-dependent diabetes mellitus (non-IDDM type II diabetes).

18. A pharmaceutical composition according to claim 15 or 16, wherein said hormone is human growth hormone (HGH) and the composition is suitable for the treatment of disorders in which HGH is involved.

19. A pharmaceutical composition according to claim 15 or 16, wherein said hormone is epidermal growth factor (EGF) and the composition is suitable for the treatment of disorders involving EGF.

20. A compound of the formula

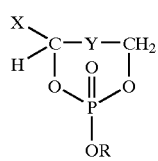

(I)

wherein

Y is —(CH$_2$)$_m$—, —CH(OH)— or —C(=O)—, and m is 1–3;

X is H, alkyl, —CH$_2$OH—, CH$_2$Oacyl or —CH$_2$acyl; and

R is H, a cation, alkyl or optionally substituted aryl; provided that:

when R is phenyl, Y is not —(CH$_2$)$_m$, and said compound is not one of (i) Cyclic dihydroxyacetone phosphate, (ii) 1,3,-cyclic propanediol phosphate (iii) 1,3-cyclic glycerophosphate, (iv) 2-methoxy-2-oxo-1,3,2-dioxaphospholane.

21. A compound of the formula

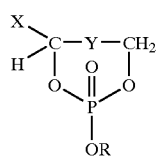

(I)

wherein

Y is —(CH$_2$)$_m$—, —CH(OH)— or —C(=O)—, and m is 1–3;

X is H, alkyl, —CH$_2$OH—, CH$_2$Oacyl or —CH$_2$acyl; and

R is H, a cation, alkyl or optionally substituted aryl;

provided that when Y is —(CH$_2$)$_m$—, m=0, and R is H or cation, X is not CH$_2$Oacyl; with the exception of the following compounds:

(i) compounds wherein Y is —(CH$_2$)$_m$—, m is 0, X is CH$_3$, —CH$_2$OH or CH$_2$Oacyl wherein acyl is a saturated carboxylic acyl with more than 12 carbon atoms, and R is H or a cation;

(ii) compounds wherein Y is —(CH$_2$)$_m$—, m is 1, X is H and R is H, a cation or phenyl; and (iii) compounds wherein Y is —CH(OH)—, X is H and R is H, a cation or phenyl.

22. A compound according to claim 20, selected from the group consisting of:

(i) phenyl cyclic dihydroxyacetone phosphate; and (ii) cyclic oleyl lysophosphatidic acid.

23. A method for treatment of blood malignancy comprising administering to the individual in need a therapeutically effective amount of a compound as defined in claim 21.

24. A method for treatment of breast cancer or prostate cancer comprising administering to the individual in need a therapeutically effective amount of a compound as defined in claim 20.

25. A method for the treatment of breast cancer or prostate cancer comprising administering to an individual in need a therapeutically effective amount of a compound as defined in claim 21.

26. A method according to claim 23, wherein said blood malignancy is leukemia.

27. A method according to claim 25, wherein said malignant disease is breast cancer.

28. A method for detecting abnormal conditions in vitro of a tested cell for breast cancer or blood malignancy, comprising:

(i) contacting the cell with a cyclic glycerophosphate or analog thereof (herein CGs) as defined in claim 1;

(ii) detecting the level of phosphorylation in intracellular proteins of the tested cells; and (iii) comparing said level of phosphorylation to the level of phosphorylation in intracellular proteins of normal cells following contact with said CGs, a level of phosphorylation differing from that detected in the normal cells indicating a high probability of abnormality in the tested cells.

29. A method for detecting abnormal conditions in vitro of a tested cell for breast cancer or prostrate cancer, comprising:

(i) contacting the cells with a cyclic glycerophosphate or analog thereof (herein CGs) as defined in claim 2;

(ii) detecting the level of phosphorylation in intracellular proteins of the tested cells; and (iii) comparing said level of phosphorylation to the level of phosphorylation in intracellular proteins of normal cells following contact with said CGs, a level of phosphorylation differing from that detected in the normal cells indicating a high probability of abnormality in the tested cells, wherein said compound is as defined in claim 1.

30. A method for treatment of prostate cancer or breast cancer, comprising administering to an individual in need thereof a therapeutically effective amount of a composition as defined in claim 1.

* * * * *